United States Patent
Wang (10) Patent No.: US 7,908,905 B2
(45) Date of Patent: Mar. 22, 2011

(54) RHEOMETER ALLOWING DIRECT VISUALIZATION OF CONTINUOUS SIMPLE SHEAR IN NON-NEWTONIAN FLUID

(75) Inventor: Shi-Qing Wang, Akron, OH (US)

(73) Assignee: The University of Akron, Akron, OH (US)

( * ) Notice: Subject to any disclaimer, the term of this patent is extended or adjusted under 35 U.S.C. 154(b) by 482 days.

(21) Appl. No.: 11/997,162

(22) PCT Filed: Aug. 31, 2006

(86) PCT No.: PCT/US2006/033969
§ 371 (c)(1),
(2), (4) Date: May 29, 2008

(87) PCT Pub. No.: WO2007/027850
PCT Pub. Date: Mar. 8, 2007

(65) Prior Publication Data
US 2009/0133477 A1      May 28, 2009

Related U.S. Application Data (60) Provisional application No. 60/712,936, filed on Aug. 31, 2005.

(51) Int. Cl.
*G01N 11/00* (2006.01)
(52) U.S. Cl. .................................................. 73/54.01
(58) Field of Classification Search .................. 73/54.01
See application file for complete search history.

(56) References Cited

U.S. PATENT DOCUMENTS

| 5,836,872 A | 11/1998 | Kenet et al. |
| 6,341,190 B1 | 1/2002 | Summersgill et al. |
| 6,733,611 B2 | 5/2004 | Hayashi et al. |

OTHER PUBLICATIONS

Kabla, A. & Debregeas, G. Local stress relaxation and shear banding in a dry foam under shear. Phys. Rev. Lett. 90, 258303 (2003).
Chan, C.L. & Woon, W.Y. Shear banding in mesoscopic dusty plasma liquids Phys. Rev. Lett. 93, 220602 (2004).
Salmon, J.B. et al. Velocity profiles in shear-banding wormlike micelles. Phys. Rev. Lett. 90, 228303 (2003).
Tapadia, P. & Wang, S.Q. Yieldlike constitutive transition in shear flow of entangled polymeric fluids. Phys Rev. Lett. 91, 198301 (2003).
Menezes, E.V. & Graessley, W.W. Nonlinear rheological behavior of polymer systems for several shear-flow histores. J. Polymer Sci.: Polymer Phys. Ed. 20, 1871-1833 (1982).
Bercea, m., Peiti, C., Simionescu, B. & Navard, P. Shear rheology of semidilute poly(methyl methacrylate) solutions. Macromolecules 26, 7095-7096 (1993).
Pattamaprom, C. & Larson, R.G. Constraint release effects in monodisperse and bidisperse polystyrenes in fast transient shearing flows. Macromolecules 34, 5229-5237 (2001).
Mooney, M. & Ewart, R.H. The conicylindrical viscometer. Physica 5, 350-354 (1934).
Macosko, C.W. Rheology: Principles, Measurements, and Applications (Wiley-VCH, New York, 1994).

(Continued)

*Primary Examiner* — Hezron Williams
*Assistant Examiner* — Rodney T Frank
(74) *Attorney, Agent, or Firm* — Joseph J. Crimaldi; Roetzel & Andress (57) ABSTRACT

The present invention is directed to an improved rheometer which provides direct visualization, and to a rheometer that can be used in conjunction with shearing devices, such as rotational, torsional, sliding plate, and other type rheometers.

2 Claims, 10 Drawing Sheets

OTHER PUBLICATIONS

Marrucci, G.J. Dynamics of entanglements: A nonlinear model consistent with the Cox-Merz rule. J. Non Newt. Fluid Mech. 62, 279-289 (1996).

Smith, D.E., Babcock, H.P. & Chu, S. Single-polymer dynamics in steady shear flow. Science 283, 1724-1727 (1999).

Bent, J. et al. Neutron-mapping polymer flow: Scattering, flow visualization, and molecular theory. Science 301, 1691-1695 (2003).

Ferry, J.D. Viscoelastic Properties of Polymers, 3rd ed. (Wiley, New York, 1980).

M. Doi, S.F. Edwards, The Theory of Polymer Dynamics 2nd ed. (Clarendon Press, Oxford, 1988).

Graessley, W.W. The Entanglement Concept in Polymer Rheology. Adv. Polym. Sci. 16, 1-179 (1974).

Tapadia, P. & Want, S.Q. Nonlinear flow behavior of entangled polymer solutions: Yieldlike entanglement-disentanglement transition. Macromolecules 37, 9083-9095 (2004).

Hu, H., Larson, R.G. & Magda, J. Measurement of wall-slip-layer rheology in shear-thickening wormy micelle solutions. J. Rheol. 46, 1001-1021 (2002).

RHEOMETER ALLOWING DIRECT VISUALIZATION OF CONTINUOUS SIMPLE SHEAR IN NON-NEWTONIAN FLUID

This work is supported, in part, by ACS-PRF grant (40596-AC7) and NSF grant (CTS-0115867). The United States government may have certain rights to the invention or inventions herein.

FIELD OF THE INVENTION

The present invention is directed to an improved rheometer which provides direct visualization, and to a rheometer that can be used in conjunction with shearing devices, such as rotational, torsional, sliding plate, and other type rheometers.

BACKGROUND OF THE INVENTION

Rheometers are used to determine the flow characteristics or behavior of rubbers, plastics, elastomers, and other polymers and viscous materials. Rheological measurements have for decades proceeded without any visualization of the field to which materials are subjected, particularly polymeric materials. The flow of complex materials is an example of nonlinear phenomena in nature. Structured fluids such as foams, colloids, micelles, granular materials and polymers display intricate dynamic behavior that is still defying complete description. Simple fluids show Newtonian behavior such as constant viscosity so that the shear stress $\sigma$ is linearly proportional to shear rate ($\dot{\gamma}$).

SUMMARY OF THE INVENTION

The present invention is directed to an improved rheometer which provides direct visualization, and to a rheometer that can be used in conjunction with shearing devices, such as rotational, torsional, sliding plate, and other type rheometers.

In one embodiment, the present invention relates to a rheometry device comprising: an optically clear plate; a metallic cone having a longitudinal axis in a perpendicular relation to the plate and the conical surface being in an acute angular relation to a surface of the plate, wherein the cone is free to rotate about its longitudinal axis, and wherein the plate is stationary; an optically clear barrier occupying a perimeter about the plate and the cone such that the space between the plate and the cone is visible; at least one laser; wherein a beam of the laser can be directed perpendicularly through the optically clear plate and impinging the cone surface; and at least one camera in a generally perpendicular relation to the longitudinal axis of the cone and directed to a region of space between the plate and the cone.

In another embodiment, the present invention relates to a process for conducting rheometric measurements, comprising the steps of: providing an optically clear plate; providing a metallic cone having a longitudinal axis in a perpendicular relation to the plate and the conical surface being in an acute angular relation to a surface of the plate, wherein the cone freely rotates about its longitudinal axis, and wherein the plate is stationary; providing a liquid contained between the cone and plate; providing at least one particle suspended in the liquid; providing at least one laser; wherein a beam of the laser is directed perpendicularly through the optically clear plate and impinging the cone surface; providing at least one camera in a generally perpendicular relation to the longitudinal axis of the cone and directed to a region of space between the plate and the cone containing one or more of the provided particles; collecting data from the at least one camera; converting the data to velocity as a function of time; and recording the data.

BRIEF DESCRIPTION OF THE DRAWINGS

FIG. 2 is a series of plots showing: (A) growth upon startup shear at shear rate 5 $s^{-1}$ of both shear and normal stresses ($\sigma$ and N1 respectively); (B) the velocity profiles of the well-entangled 10% PBD solution for shear rates 0.05 and 0.1 $s^{-1}$ at any time, where the straight lines indicate linear profiles; and (C) the velocity profiles for shear rate 5 $s^{-1}$, at initial (circles), transient (diamonds), quasi-steady state (open squares) and steady state (squares), as measured on the video monitor where the frame rate is 15 frames per second and the velocity profile for the pure oligomeric solvent, which is a Newtonian liquid, is also depicted in the plus filled squares.

DETAILED DESCRIPTION OF THE INVENTION

The present invention is directed to an improved rheometer which provides direct visualization, and to a rheometer that can be used in conjunction with shearing devices, such as rotational, torsional, sliding plate, and other type rheometers.

In one embodiment, a method according to the present invention uses direct visualization of the flow field involved in rheometric measurement. Due in part to this feature, the present invention enables the probing of a velocity profile in real time during controlled-rate shear. Due to the present invention, it has been determined that when the velocity gradient is non-uniform, the velocity profile changes significantly over time upon a controlled-rate startup shear in the stress plateau region. This finding questions the widely-employed protocol of imposing controlled-rate shear as an effective method to depict constitutive flow behavior of entangled polymeric liquids and casts doubt on the existing knowledge of constitutive behavior of this large class of highly commercially valuable materials.

Using the particle-tracking-velocimetric technique of the present invention, one can demonstrate that, for an entangled polymer solution, the velocity profile in a simple shear ($\dot{\gamma}$) deviates strongly from the anticipated linearity, whereas these structured fluids appear to show a possible discontinuous relationship between σ and $\dot{\gamma}$. The velocity gradient is non-uniform and the velocity profile changes significantly over time upon a controlled-rate startup shear in the stress plateau region that is commonly encountered for entangled polymers. This would appear to invalidate the method of controlled-rate shear that is widely employed to probe constitutive flow behavior of various complex fluids.

It has also be found that the velocity profile evolves in time, linear at the startup of shear, and attains a maximum deviation from the linearity in the transient before settling to the steady state where the velocity gradient varies explicitly along the sample thickness. In one embodiment, the process of the present invention can be used to evaluate how several hundred million tons of plastic materials get processed into final articles. This can help produce stronger plastic products ranging from grocery/garbage bags to milk bottles and children toys, in addition to lowering the costs associated with making/producing a wide range of plastic/polymer products.

The method and apparatus of the present invention can be applied to any rheometer or shearing device where there is a need for flow visualization of the velocity profile in real time during both controlled-rate and controlled-stress shear. The present invention can also be used to provide a visual input or it can be used in combination with a typical rheometer to provide a measurement of the viscosity of the particular material being evaluated.

Figure 1:
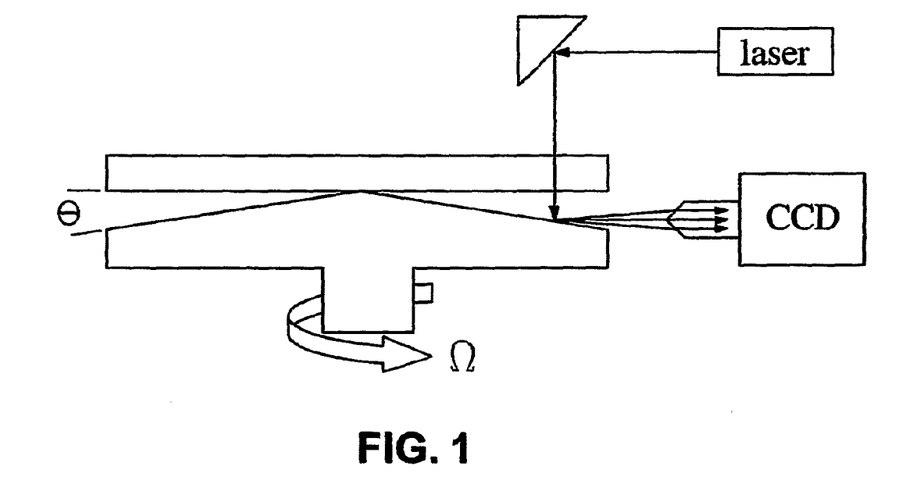
FIG. 1 is a schematic of the setup of the particle tracking velocimetry, where the upper stationary plate is made of transparent glass, the lower rotating cone made of steel and $\theta=5°$.

A cone-plate shear cell is a particularly convenient device used to explore the constitutive behavior of structured liquids including entangled polymers because it allows continuous simple shear to be produced. This device generates uniform simple shear flow for both Newtonian and non-Newtonian liquids, provided that their constitutive relations are invertible. Regarding polymeric liquids as simple fluids, researchers routinely shear their samples in a cone-plate flow cell by imposing an angular velocity Ω on one of the two surfaces as shown in FIG. 1. A constitutive relation is determined by measuring the corresponding torque required to maintain Ω, assuming that a uniform shear rate $\dot{\gamma}=\Omega/\theta$ would be created across the sample thickness. This mode of imposing a constant surface velocity has become a standard protocol known as controlled-rate shear and was thought to generate a linear velocity profile in the gap independent of the constitutive behavior.

Monodisperse entangled polymer solutions were found to display a discontinuous flow transition under constant applied shear stress at a critical value σc, where the resulting apparent shear rate was almost three orders of magnitude higher than its value below σc. The controlled-rate measurements only turned up a smooth continuous flow curve with a characteristic stress plateau. Thus, depending on which variable (surface velocity vs. applied force) is controlled in generating the simple shear, there exist two different flow curves for the same sample.

FIG. 1 shows a schematic of the setup of the particle tracking velocimetry, where the upper stationary plate is made of transparent glass, the lower rotating cone made of steel and θ=5°. The apparatus allows for a view of the velocity field at a specific radial position in the gap, and affords good spatial and time resolutions. The device of FIG. 1 can be used as an accessory to a commercial rheometer, allowing in-situ observations along with rheological information.

The entangled polymer solution evaluated is a 10 weight percent 1,4-polybutadiene (PBD) solution, made of a high weight PBD of $M_w=1.24\times10^6$ g/mol and $M_w/M_n=1.2$ from (Polymer Source Inc. P1445-Bd) dissolved in a phenyl-terminated oligomeric butadiene of $M_n=1.0$ K (Aldrich 200417). For the particle tracking purpose, the sample is seeded with silver-coated particles of 10 micron diameter (Dantec Dynamics HGS-10) at a low level of ca. 200 ppm. A controlled-rate shear rheometer (ARES) equipped with a cone-plate assembly of 25 mm diameter is employed to make velocity profile measurements, where the cone angle θ is 5°.

The particle tracking velocimetry of the present invention comprises sending a laser beam along the velocity gradient direction through the gap between cone and plate and videotaping the illuminated moving particles over time with a CCD camera facing the gap as shown in FIG. 1. A thin film surrounds the meniscus to allow focus of a tele-microlens onto the interior illuminated particles. The negligible perturbation of the confining film on the simple shear flow inside the cone-plate has been both estimated and experimentally verified.

Figure 2A:
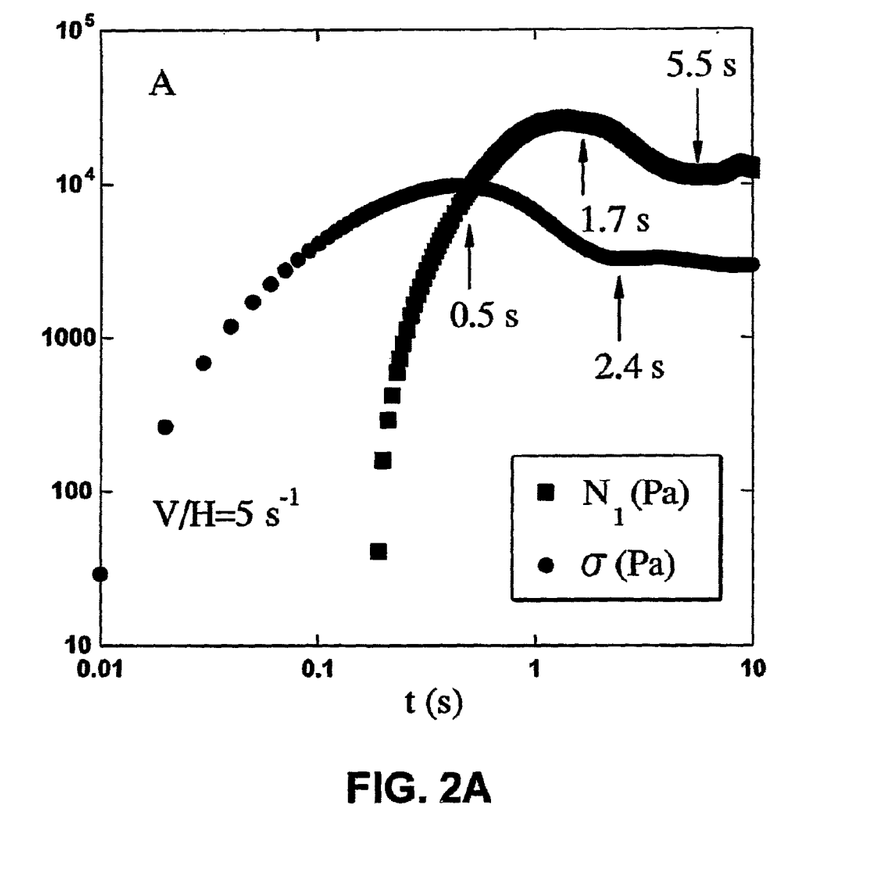

We examine the flow field in the cone-plate cell at three imposed shear rates of 0.05, 0.1 and 5 $s^{-1}$. These rates respectively correspond to the Newtonian region, the region just before the stress plateau, and the region well inside the stress plateau. At the two low values of $\dot{\gamma}=\Omega/\theta$, i.e., two low values of angular velocity Ω, the stresses grow monotonically. But at 5 $s^{-1}$, FIG. 2A shows non-monotonic behavior in both shear (σ) and normal ($N_1$) stresses, where σ first grew to its maximum at t=0.5 and then dropped to its steady state value at t=2.4 s, meanwhile the first normal stress $N_1$ reached its maximum at t=1.7 s and approached its steady state around t=5.5 s. The feature of overshoots (especially of σ) is well known for entangled polymers under high shear and has been understood for decades to be the flow characteristic of a uniformly sheared sample.

Figure 2B:
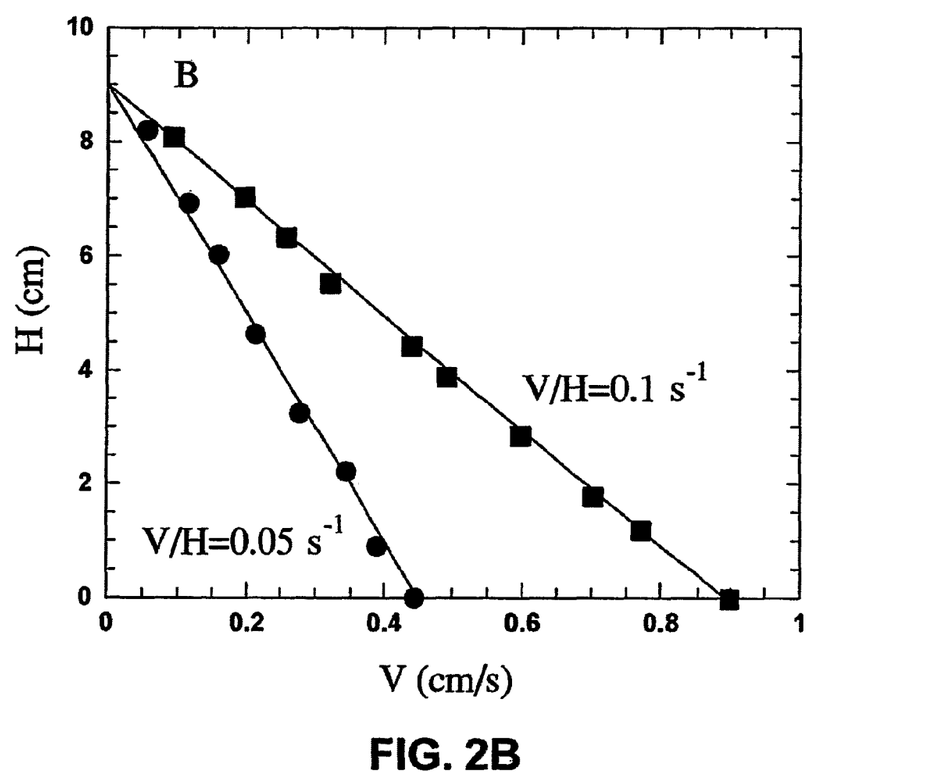
Figure 2C:
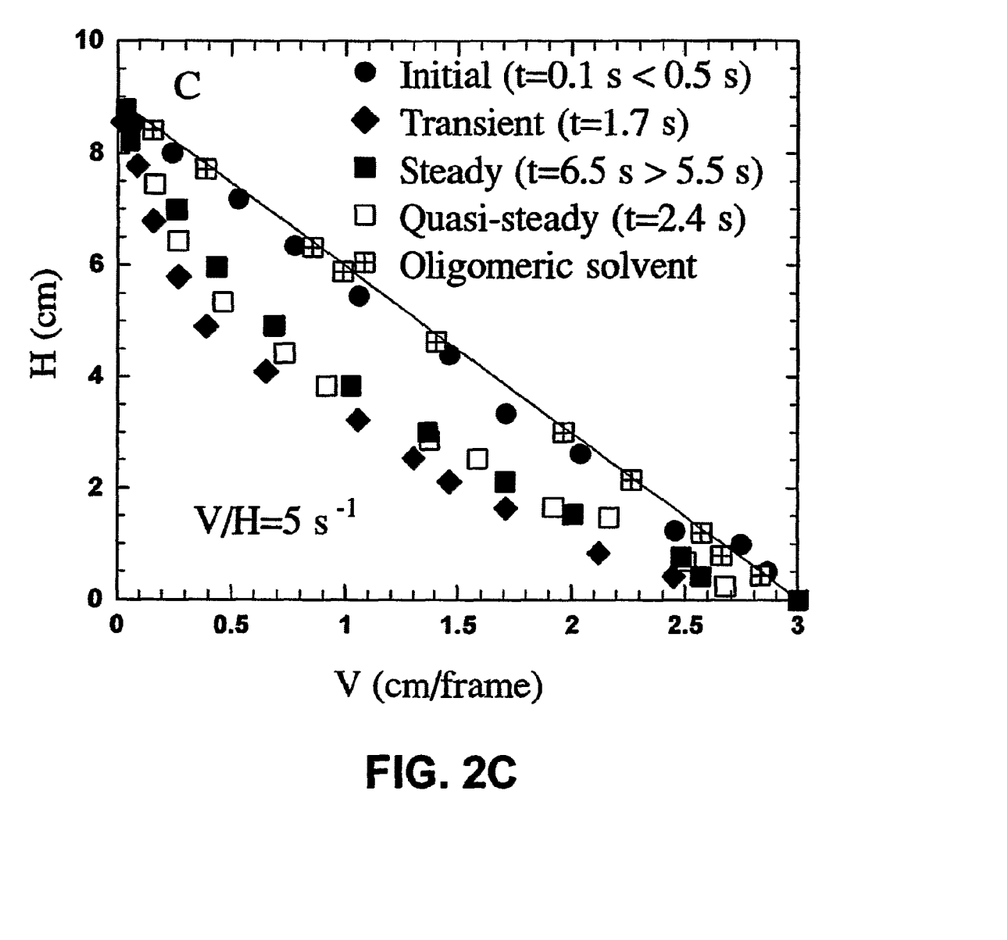

As shown in FIG. 2B, particle track velocimetric (PTV) measurements demonstrate that the velocity gradients are essentially uniform along the gap at the low shear rates. At the high shear rate of 5 $s^{-1}$, i.e., when the angular velocity of the rotating cone is set to Ω=5θ=0.44 rad/s, the velocity field no longer varied linearly across the gap as shown in FIG. 2C. In contrast, when a Newtonian oligomeric butadiene liquid (which was used as the solvent for the 10% PBD solution) is subjected to the same shearing condition at 5 $s^{-1}$, a constant value equal to the preset value prevails at all times in every layer in the gap, as shown by the plus-filled squares in FIG. 2C. The actual gap distance H involved in FIGS. 2B and 2C was ca. 0.9 mm (i.e., about 10 mm from the cone center) and was 9 cm on the video monitor where the measurements were taken.

This first set of particle tracking velocimetric observations reveals that the entangled polymeric liquid is in a state of frustration when subjected to an average shear rate that falls in the window of flow discontinuity, from a shear rate of 0.2 to 40 $s^{-1}$. In other words, the entangled chains prefer to be sheared either at 0.2 $s^{-1}$ and lower or 40 $s^{-1}$ and higher. When the imposed angular velocity Ω is such that Ω/θ=5 $s^{-1}$, falling in the middle of this window, the system apparently satisfied this boundary condition by sampling a spectrum of shear rates. The local shear rate at the top stationary plate was smaller than ⅙ of the prescribed value of 5 $s^{-1}$, whereas the local shear rate at the rotating cone essentially doubled from 5 to 10 $s^{-1}$.

Equally interesting and important, the velocity profile evolved over time. Corresponding to the characteristic times indicated in FIG. 2A, one can show that the velocity gradient is initially constant across the gap up to the point of the stress maximum, i.e., up to t=0.5 s. The maximum deviation from this linear velocity profile occurred around the maximum of $N_1$, i.e., at around t=1.7 s. The eventual steady state possessed a weaker nonlinear profile, as shown in FIG. 2C, which was not reached until after $N_1$ had stabilized at 5.5 s. In other words, the profile was still evolving at t=2.4 s when the shear stress σ had already stabilized.

Apart from these explicit rheological and PTV measurements in FIG. 2, the process of the present invention provides a direct visual impression of the variations of the velocity profile across the gap with time.

Figure 3:
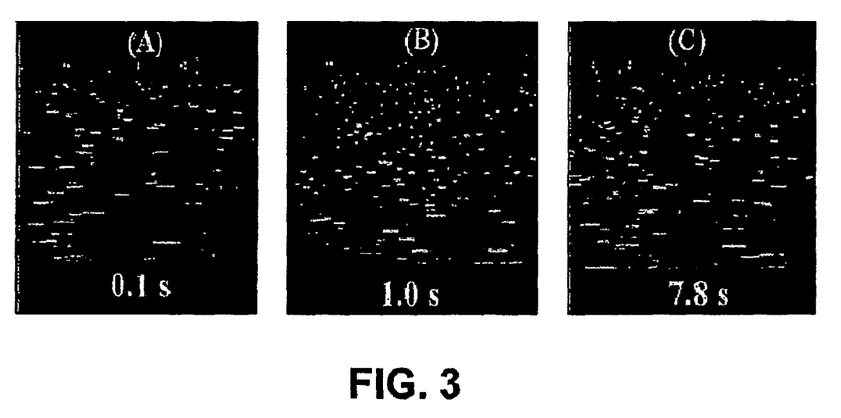
FIG. 3 represents still pictures from video recording of the illuminated moving particles at (A) initial (t=0.1), (B) transient (t=1.0 s) and (C) steady (t=7.8 s) states for an imposed apparent shear rate of $\Omega/\theta=10$ $s^{-1}$, where the distance between the two horizontal lines, H, is again about 0.9 mm. Only the particles in focus yield the brightest spots and streaks.

FIG. 3 shows three snapshots of the particle movements for a shear rate of $\Omega/\theta=10$ s$^{-1}$ as seen from the gap at three characteristic times corresponding to initial, transient and steady states. The exposure time of the CCD camera is $\Delta t=1/60$ s. The still pictures from video recording show the illuminated moving particles at (A) initial (t=0.1), (B) transient (t=1.0 s) and (C) steady (t=7.8 s) states for an imposed apparent shear rate of $\Omega/\theta=10$ s$^{-1}$, where the distance between the two horizontal lines, H, is about 0.9 mm. Only the particles in focus yield the brightest spots and streaks. From the length $\Delta x$ of the streak generated by the moving light-scattering particle, one can compute the speed of the particle according to $V=\Delta x/\Delta t$. Thus, the streak length is directly proportional to the particle speed V since $\Delta t$ is fixed during the video recording. The three pictures clearly show different streak length variations along the gap, indicating different velocity profiles similar to those measured in FIG. 2 for 5 s$^{-1}$ at the different times, although in real time play, it is easier to watch the particle motion at a lower shear rate of $\Omega/\theta=2.5$ s$^{-1}$.

The particle tracking velocimetric method of the present invention provides flow responses of entangled polymer solutions in a commonly employed shear device of cone-plate, examines the controlled-rate shear measurements that assume a uniform velocity gradient in space and examines the long-standing research tradition in the area of non-Newtonian flow of complex materials.

The following references are incorporated herein by reference in their entireties:

(1) Kabla, A. & Debregeas, G. Local stress relaxation and shear banding in a dry foam under shear. Phys. Rev. Lett. 90, 258303 (2003).

(2) Chan, C. L. & Woon, W. Y. Shear banding in mesoscopic dusty plasma liquids Phys. Rev. Lett. 93, 220602 (2004).

(3) Salmon, J. B. et al. Velocity profiles in shear-banding wormlike micelles. Phys. Rev. Lett. 90, 228303 (2003).

(4) Tapadia, P. & Wang, S. Q. Yieldlike constitutive transition in shear flow of entangled polymeric fluids. Phys Rev. Lett. 91, 198301 (2003).

(5) Menezes, E. V. & Graessley, W. W. Nonlinear rheological behavior of polymer systems for several shear-flow histories. J. Polymer Sci.: Polymer Phys. Ed. 20, 1817-1833 (1982).

(6) Bercea, M., Peiti, C., Simionescu, B. & Navard, P. Shear rheology of semidilute poly(methyl methacrylate) solutions. Macromolecules 26, 7095-7096 (1993).

(7) Pattamaprom, C. & Larson, R. G. Constraint release effects in monodisperse and bidisperse polystyrenes in fast transient shearing flows. Macromolecules 34, 5229-5237 (2001).

(8) Mooney, M. & Ewart, R. H. The conicylindrical viscometer. Physica 5, 350-354 (1934).

(9) Macosko, C. W. Rheology: Principles, Measurements, and Applications (Wiley-VCH, New York, 1994).

(10) Marrucci, G. J. Dynamics of entanglements: A non-linear model consistent with the Cox-Merz rule. J. Non Newt. Fluid Mech. 62, 279-289 (1996).

(11) Smith, D. E., Babcock, H. P. & Chu, S. Single-polymer dynamics in steady shear flow. Science 283, 1724-1727 (1999).

(12) Bent, J. et al. Neutron-mapping polymer flow: Scattering, flow visualization, and molecular theory. Science 301, 1691-1695 (2003).

(13) Ferry, J. D. Viscoelastic Properties of Polymers, 3rd ed. (Wiley, New York, 1980).

(14) M. Doi, S. F. Edwards, The Theory of Polymer Dynamics, 2nd ed. (Clarendon Press, Oxford, 1988).

(15) Graessley, W. W. The Entanglement Concept in Polymer Rheology. Adv. Polym. Sci. 16, 1-179 (1974).

(16) Tapadia, P. & Wang, S. Q. Nonlinear flow behavior of entangled polymer solutions: Yieldlike entanglement-disentanglement transition. Macromolecules 37, 9083-9095 (2004).

(17) Hu, H., Larson, R. G. & Magda, J. Measurement of wall-slip-layer rheology in shear-thickening wormy micelle solutions. J. Rheol. 46, 1001-1021 (2002).

Liquids that possess a linear relationship between shear stress σ and shear rate $\dot\gamma$ are known as Newtonian fluids, where the proportionality constant is viscosity η. Polymeric liquids, made of long linear chains that form entanglement since they cannot pass over one another without breaking, are an important class of non-Newtonian fluids, whose viscosity η takes a finite time to reach the steady state value and decreases with $\dot\gamma$. This widely known shear thinning behavior was thought to occur gradually due to increased chain alignment in shear that leads to disentanglement. If the chain disentanglement event was not to occur catastrophically in shear flow as agreed upon by the current consensus, shear thinning would take place homogeneously in every layer across the sample thickness. Then, just as in the case of Newtonian fluids, imposition of V on one surface over the other stationary surface in a parallel-plate device of gap H would indeed result in a homogeneous flow with shear rate V=H prevailing in every layer.

Many structured materials, such as micellar solutions, dense suspensions, foams, liquid crystals, soft gels and glasses, granular fluids, and metals, respond to large external deformation catastrophically: The imposed shear deformation or rate of deformation can produce a spatially nonhomogeneous distribution of different states across the sample thickness. This is commonly known as shear banding. Entangled model polymer solutions have also recently been found to show a spatial variation in the shear rate measured across the sample thickness in startup shear. This finding makes it rather difficult to establish a constitutive relationship between σ and $\dot\gamma$ through rheological measurements. It also challenges the currently favored version of the theoretical description of entangled polymers in shear flow that arose from a decade of theoretical efforts based on the de Gennes' visualization of snakelike motion of a test chain within the Edwards' tube picture. Furthermore, it calls for an reexamination of previous experimental studies of similar entangled polymer solutions.

Inspired by the previous results on continuous shear behavior of entangled polymer solutions, we have carried out further experiments in the present work to decipher how chains actually negotiate with one another to establish any new topological relationship during shear. Specifically, in this work, we apply large-amplitude oscillatory shear (LAOS) to illustrate some intriguing flow behavior of entangled liquids by using an effective particle-tracking velocimetric method to determine the velocity profile in LAOS. The results indicate that chain disentanglement, as the cause of shear thinning, also occurs inhomogeneously in space in LAOS.

The entangled polymer solutions under examination are a previously prepared and studied 10 wt. % 1,4-polybutadiene (PBD) solution, made of a high weight PBD of $M_w=1:2\times10^6$ g=mol and $M_w/M_n=1:18$ from Polymer Source, Inc., dissolved in a phenyl-terminated oligomeric butadiene (oBD) of $M_n=1:0$ kg=mol (Aldrich 20041-7), and a newly made 10% PBD solution of a monodisperse PBD of $M_w=740$ kg/mol (made at Bridgestone) in a monodisperse oBD of Mw=4 kg/mol (made at Goodyear). For the particle-tracking purpose, the sample was seeded with silver-coated particles of 10 μm diameter (Dantec Dynamics HGS-10) at a level of several hundred parts per million. A strain-controlled shear rheometer equipped with a cone-plate assembly of 25 mm diameter was employed in this study.

Figure 4:
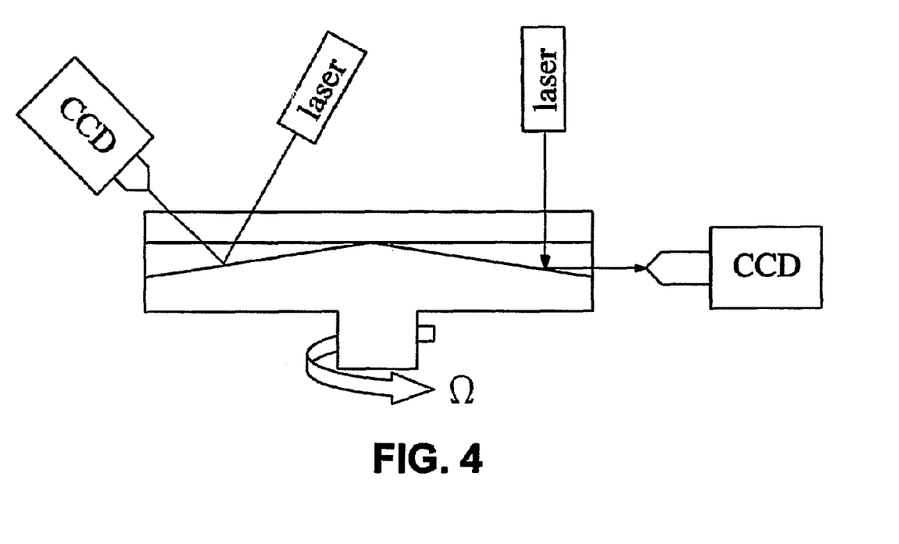
FIG. 4 is a schematic of the setup of the particle tracking velocimetry according to another embodiment of the present invention.

Our particle-tracking velocimetry, as illustrated in FIG. 4, consists of sending a laser beam either along the velocity gradient direction or at an angle to the shearing surface and videotaping the illuminated moving particles with a black-white CCD camera (with minimum 0.3 lx and maximum 30 frames per second) that is mounted with a DIN objective (3:2×) through an adaptive tube (Edmund Optics: U54-868). In scheme A, a transparent film surrounds the meniscus to allow focus of a telemicrolens onto the interior. The perturbation of the confining film on the simple shear flow inside the cone-plate cell can be evaluated and is removable by employing scheme B. In the present work, scheme A was set up for an advanced rheometrics expansion system, where a bottom cone rotates against a fixed upper plate; scheme B was set up for a Bohlin CVOR rheometer (Malvern Instruments) where an upper cone rotates. Results from both protocols will be presented below.

Let us consider oscillatory shear by sandwiching a sample between cone and plate as shown in FIG. 4, where the cone would make an oscillatory torsional motion against the fixed plate, as described by angular displacement $\phi(t)=\phi_0 \sin(\omega t)$ and velocity by $\Omega=\phi_0\omega \cos(\omega t)$. The shear strain is usually taken to be uniform across the gap equal to $\gamma_0=X_0(r)/h(r)\approx\phi_0/\theta$, with $X_0(r)=\phi_0 r_o$, where $h(r)=r \tan \theta \approx r\theta$ is the gap distance at r. At low amplitudes $\gamma_0 \ll 1$, the storage modulus G' and loss modulus G" were obtained as a function of ω, indicating that the overall chain relaxation rate, i.e., the crossover frequency $\omega_c$ (at which G'=G"), was around 0:07 rad/s for the entangled liquid. When the oscillatory shear was applied at frequencies $\omega > \omega_c$, the entangled chains would tend to deform and orient affinely without being able to relax significantly during the shear reversal in each cycle.

Figure 5:
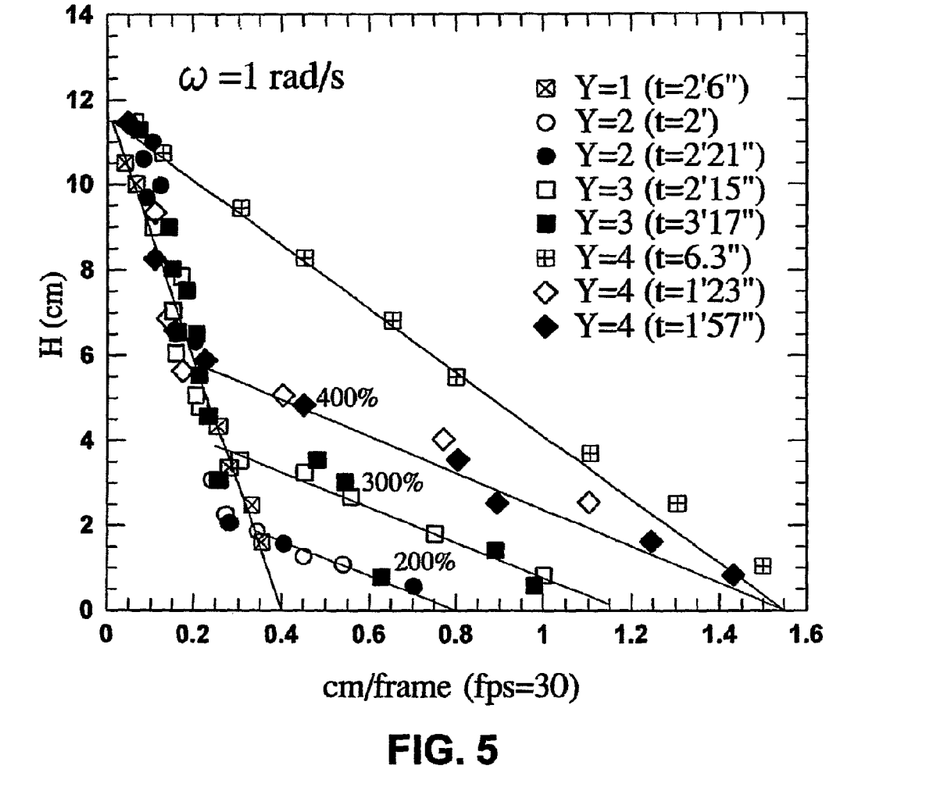
FIG. 5 is a set of plots showing velocity profiles in large amplitude oscillatory shear of various samples as measured according to an embodiment of the present invention.

We subjected the sample to LAOS for a sufficiently long time at $\omega=1$ rad/s $>\omega_c$ to illustrate the effect of LAOS on the molecular reorganization. In the first cycle, the shear deformation was uniform across the gap, and such a uniform deformation also prevailed for $\gamma_0 \leq 1$ even at long times. But, over time, something dramatic took place. One key result of our particle-tracking velocimetric measurements is shown in FIG. 5. As one way to visualize the effect of LAOS, we analyzed the velocity field at the instant of the maximum Ω of the rotating cone. The video recording can also be analyzed at any other moments during each cycle. The measurements typically involve playing the movie frame by frame at a fixed rate of 30 frames per second using MGI VIDEOWAVE 4 software for about one to three frames and measuring, on a computer monitor, the displacement of the traced particles over these frames in the different layers across the sample thickness. The time resolution is therefore as good as about 0.1 s. In contrast to the linear velocity profile seen for $\gamma_0=1$ and at the beginning for $\gamma_o=4$, the steady state velocity profiles are highly nonlinear. The actual gap distance H was ca. 0.9 mm (i.e., about 10 mm from the cone center) and was 12 cm on the video display, where the measurements were taken and presented in FIG. 5. The reader can access a movie showing the evolution of velocity profile for $\gamma_0=3$, based on which the open and solid squares were obtained in FIG. 5.

Figure 6:
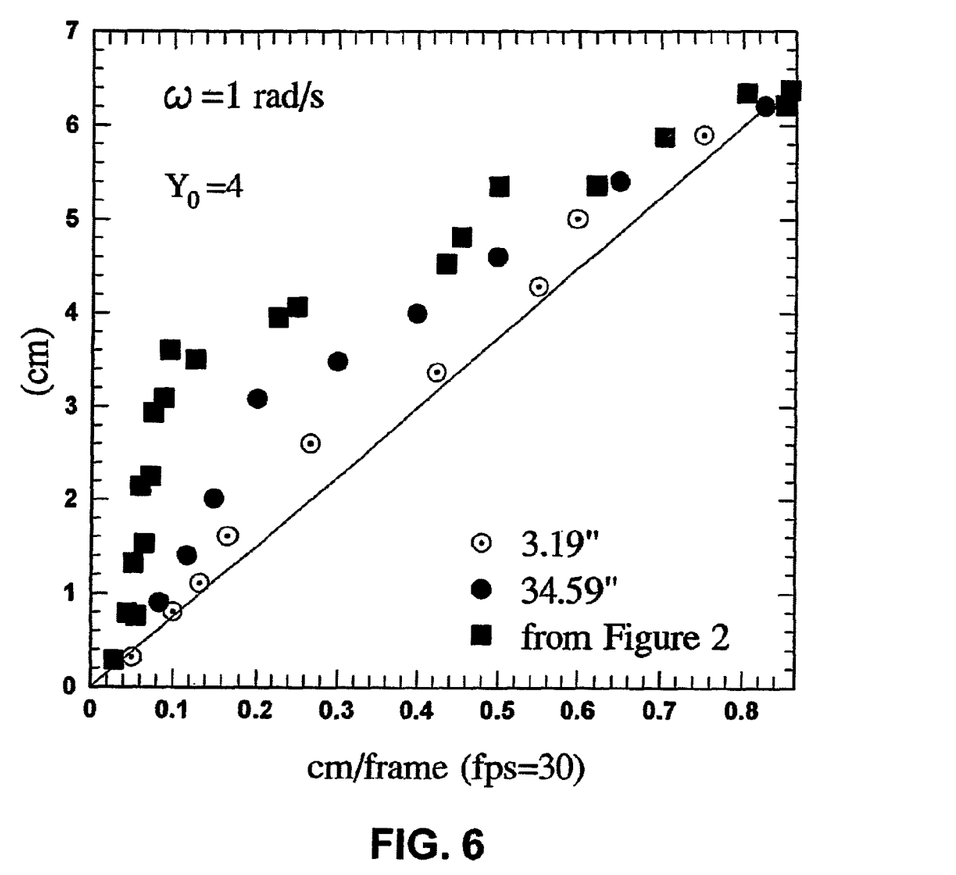
FIG. 6 is a plot of velocity data as observed using the scheme detailed in FIG. 4.

To remove the potential complications introduced by the confining film around the meniscus, we examine the velocity profile at LAOS of a different 10% PBD solution using a second rheometer from Malvern Instruments where an upper cone rotates against a fixed lower plate. Using scheme B as depicted in FIG. 4, we obtained another set of velocity profiles as shown in FIG. 6. The banding behavior is very similar to that shown in FIG. 5, and the difference arises from the difference in the makeup of these two different samples. Thus, this result indicates that there is a negligible effect at the location of observation from the stationary film surrounding the meniscus in scheme A in FIG. 4. To rule out the possibility that the observed banding would be due to a tiny stress gradient in the cone-plate setup, similar experiments have been conducted using parallel-disk shear cells, and the banding was also systematically observed.

Returning to FIG. 5, we note the banding characteristics to depend on the amplitude of the imposed strain. The peak shear rate $\gamma'_0=\omega\gamma_0$ in the "fluid" layer reached 7:2 s[31 1], whereas the "solid" top layer experienced a peak shear rate nearly tenfold smaller. In other words, the bottom layer experienced a shear strain as high as over 700%, whereas the top layer remained intact and was only undergoing deformation no greater than 100%. Upon increasing $\gamma_0$ from 2 to 4, the fractional thickness f of the fluid layer increased from ⅙ to ½, which can be described by $f=(\gamma_0-1)/6$, implying that no part of the sample would transform to a "fluid," i.e., f=0 when $\gamma_0 \leq 1$, which is indeed the case as shown in FIG. 5.

Figure 7A:
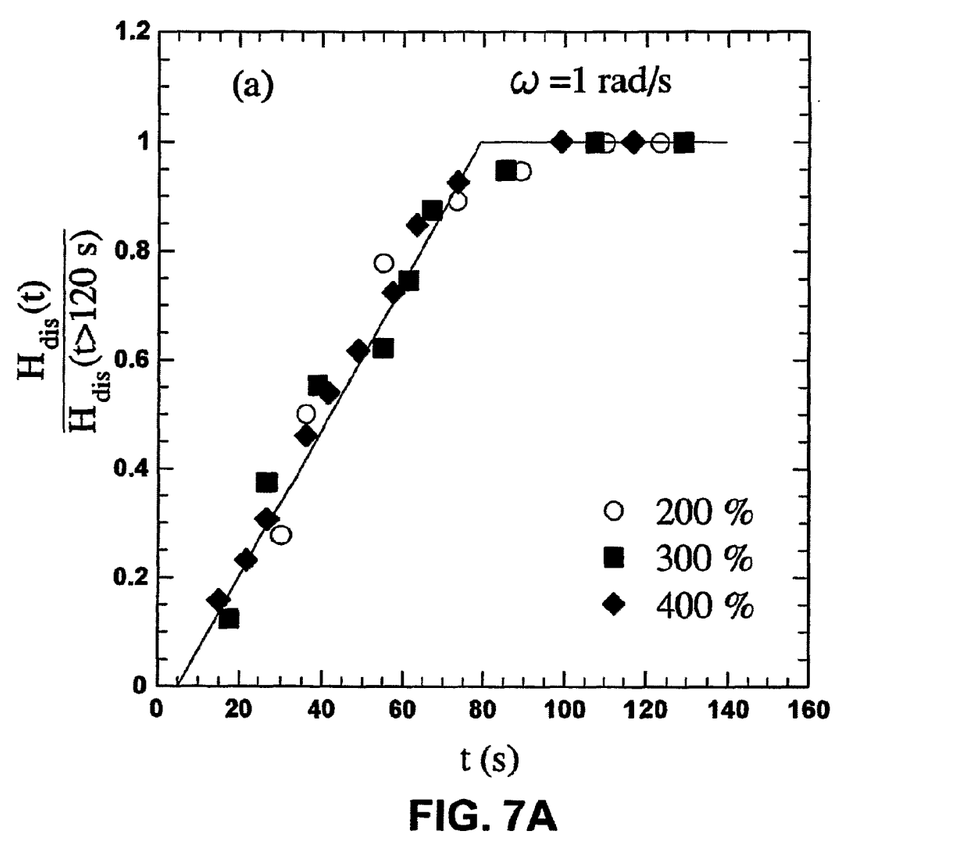
FIG. 7(A) is a plot showing the effect of varying oscillation frequency while keeping the amplitude constant.

To elucidate the dynamics of this striking phenomenon, we followed the evolution (i.e., the thickness growth) of the disentangled layer over time. The flow behavior of the fluid-like layer looks distinctly different from that of the solid-like layer according to the visual impression of the recorded video. We can simply watch how the bottom layer grows in time and stop the video play to determine its thickness at the different time intervals. We first look for any amplitude effect at a fixed oscillation frequency of $\omega=1$ rad/s. FIG. 7(a) shows that the sample reached its final state during the same time interval (ca. 100 s) regardless of the value of $\gamma_0>1$.

Figure 7B:
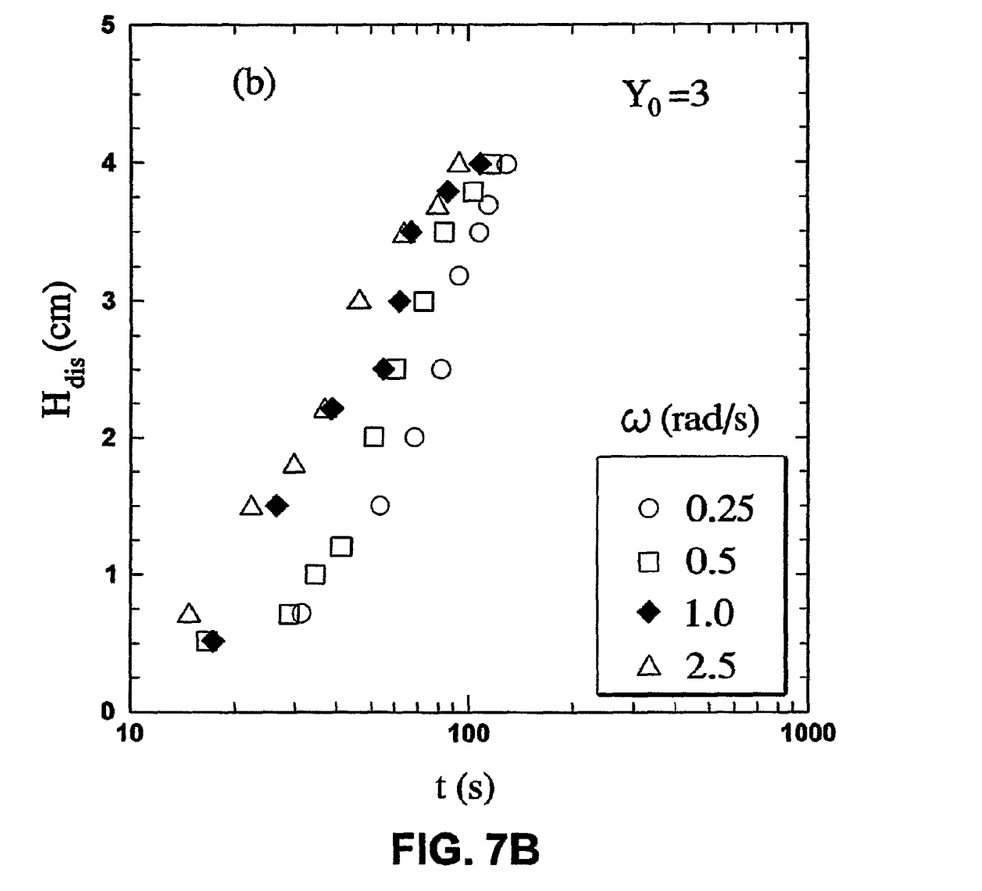
FIG. 7(B) is a set of plots showing the effect of varying oscillation frequency while keeping the amplitude constant above the chain relaxation rate of 0.07 rad/s.

We next subjected the sample to an amplitude of $\gamma_0=3$ at various oscillation frequencies that were all higher than the chain relaxation rate of $\omega_c=0:07$ rad/s. Independent of the oscillation frequency, the final thicknesses of the fluid layer all attained 4 cm on the video monitor, or ca. ⅓ of the total sample thickness, at approximately the same time, around 100 s as shown in FIG. 7B. Since ω differed by a factor of 10, in a given duration the sample had been subjected to 10 times as many cycles at $\omega=25$ rad/s as it had at $\omega=0.25$ rad/s. Conversely, the total amount of cumulative shear strain $\gamma_t$ was 10 times smaller at 0.25 than at 2.5 rad/s. FIG. 7B shows that the growth time was hardly dependent on $\gamma_t$ and ω and depended only on the time during which the sample was subjected to the LAOS at $\omega>\omega_c$, indicating that flow convection played a minor role at most. FIG. 7A further indicates that, as long as the strain amplitude was high enough (i.e., $\gamma_0>1$) to produce sufficient chain orientation, the kinetics leading to the final state were essentially the same, independent of $\gamma_0$. This behavior is true only for the present highly polydisperse sample. Monodisperse samples display a different set of phenomena.

The preceding experimental observations indicate that the entangled solution is capable of rearranging over time into different states of entanglement in the various layers in simple shear. Specifically, the LAOS produced over time a coexistence of two different states of chain entanglement, indicating that the sample could not undergo chain disentanglement and shear thinning uniformly across the sample thickness. The key controlling variable appears to be a sufficiently high level of chain orientation as determined by the amplitude of the oscillatory shear. As long as the oscillation frequency is higher than the chain relaxation rate so that the imposed LAOS is effective to produce long-lasting chain orientation, the initially well-entangled chains find themselves in a new, anisotropic environment that allows them to look for a different topological relationship. With sufficient chain orientation, the chains seem to clear out of each other's way and enter a new dynamic state of less mutual constraint in a spatially inhomogeneous fashion, where some layers absorb the imposed strain by transforming into a state of disentanglement, allowing the rest of the sample to stay in a nearly equilibrium state of entanglement. The movie shows that it actually took roughly only one period or a few seconds for the fluid layer to become visible, whereas the time required for the transformed layer to grow to its final thickness is much longer. The kinetics governing the growth was found to be insensitive to both $\omega$ and $\gamma_0$. Currently, there is no theoretical description available to account for the nucleation and growth of the disentangled state in shear oscillation. However, let us hope that the available theoretical framework can provide an adequate description of the reported phenomena.

In summary, the entangled polymer solution was found to respond to strain-controlled large-amplitude oscillatory shear by transforming partially into a state of lower viscosity and, thus, a lower level of chain entanglement. The response appears to show a state of frustration because the transformation (i.e., chain disentanglement) could not take place homogeneously as shown in FIGS. 5 and 6. The coexistence of two layers of different viscoelastic properties under a given LAOS shows that chain disentanglement nucleates unevenly in space, taking place only under the critical condition of sufficient chain orientation. Here the "nucleation" appears to occur through chain diffusion as evidenced by the observations in FIGS. 7A and 7B. Ongoing work in our lab has shown other banding features that are not observed here for the present rather polydisperse solutions. Future reports will focus on the other mechanism responsible for shear banding in LAOS.

Although the invention has been described in detail with particular reference to certain embodiments detailed herein, other embodiments can achieve the same results. Variations and modifications of the present invention will be obvious to those skilled in the art and the present invention is intended to cover in the appended claims all such modifications and equivalents.

What is claimed is:

1. A rheometry device comprising:
   an optically clear plate;
   a metallic cone having a longitudinal axis in a perpendicular relation to the plate and the conical surface being in an acute angular relation to a surface of the plate, wherein the cone is free to rotate about its longitudinal axis, and wherein the plate is stationary;
   an optically clear barrier occupying a perimeter about the plate and the cone such that the space between the plate and the cone is visible;
   at least one laser; wherein a beam of the laser can be directed perpendicularly through the optically clear plate and impinging the cone surface; and
   at least one camera in a generally perpendicular relation to the longitudinal axis of the cone and directed to a region of space between the plate and the cone.

2. A process for conducting rheometric measurements, comprising the steps of:
   providing an optically clear plate;
   providing a metallic cone having a longitudinal axis in a perpendicular relation to the plate and the conical surface being in an acute angular relation to a surface of the plate, wherein the cone freely rotates about its longitudinal axis, and wherein the plate is stationary;
   providing a liquid contained between the cone and plate;
   providing at least one particle suspended in the liquid;
   providing at least one laser; wherein a beam of the laser is directed perpendicularly through the optically clear plate and impinging the cone surface;
   providing at least one camera in a generally perpendicular relation to the longitudinal axis of the cone and directed to a region of space between the plate and the cone containing one or more of the provided particles;
   collecting data from the at least one camera;
   converting the data to velocity as a function of time; and
   recording the data.

* * * * *